Aug. 20, 1957 F. W. ANDERSON Plant Pat. 1,634

NECTARINE TREE

Filed Feb. 20, 1956

WITNESS

Addison E. Avery

INVENTOR

Frederic W. Anderson

Webster & Webster

ATTYS.

United States Patent Office

Plant Pat. 1,634
Patented Aug. 20, 1957

1,634

NECTARINE TREE

Frederic W. Anderson, Merced, Calif.

Application February 20, 1956, Serial No. 566,743

1 Claim. (Cl. 47—62)

This invention relates to a new and distanct variety of nectarine tree which bears large red clingstone fruit.

The major characteristic of the present variety of nectarine tree resides in the fact that—while there is general resemblance to the Red Grand nectarine (United States Plant Patent No. 1,060), the fruit of the instant variety ripens approximately two weeks in advance thereof.

As the Red Grand nectarine fruit has been favorably received in the commercial market, the present variety will provide such market with a comparable fruit, but in earlier season.

The harvest period of the present variety of nectarine is approximately with the Early Le Grand nectarine (United States Plant Patent No. 980), but otherwise, in comparison, substantial differences are recognized, as follows:

The fruit of the present variety is slightly smaller in size, but is more nearly round in shape, has a smoother surface, more attractive yellow under color, much more red exterior color, and more red color next to the stone.

Further, grown in the same orchard on adjacent trees, fruit of this variety has evidenced no growth cracks, while many appear on the Early Le Grand nectarine, depending of course on the season and the size of the crop.

Also, this variety has experienced considerably less bud drop after warm winters, followed by heavier sets of fruit which have been much more uniform in size and shape, and substantially less subject to split pits.

Additionally, the shoot growth of this variety is markedly shorter, heavier, and more upright; the leaves, with the same fertilizer program, being decidedly lighter in color.

Because of heavier bearing of more attractive fruit, including the smoother surface, more red exterior color, and greater uniformity in size and shape, together with a lower chilling requirement, the persent variety is much more desirable, commercially, than the Early Le Grand nectarine.

The herein claimed variety of nectarine was originated by me, in connection with a long and continuing fruit development program, as an open-pollinated seedling of the Red Grand nectarine; the variety having been originated in my experimental orchard located near Le Grand, Merced County, California.

Subsequent to its origination, and recognition by me of its novel characteristics, I asexually reproduced the variety—in my experimental orchard located as aforesaid—by top-working by budding on mature orchard trees. Subsequently, when such top workings came into bearing, they were found to carry forward all of the characteristics of the parent seedling.

Figure 1:
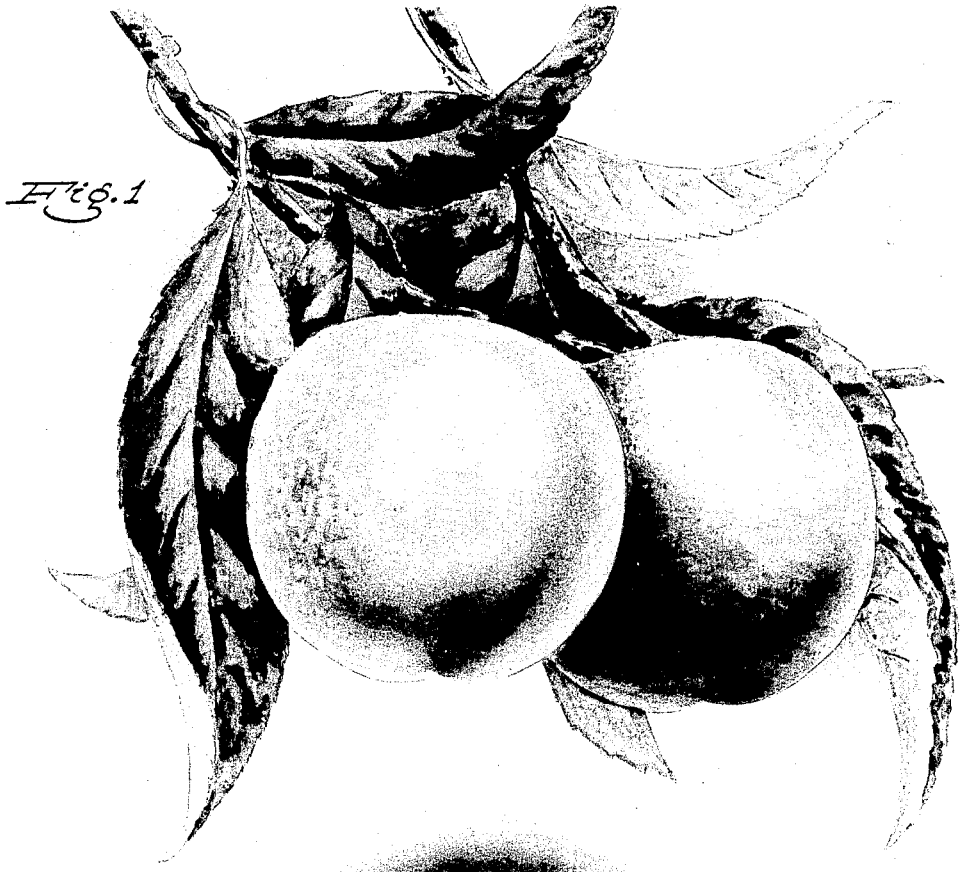
Fig. 1 is an elevation showing two of the fruit, together with twigs and leaves.
Figure 2:
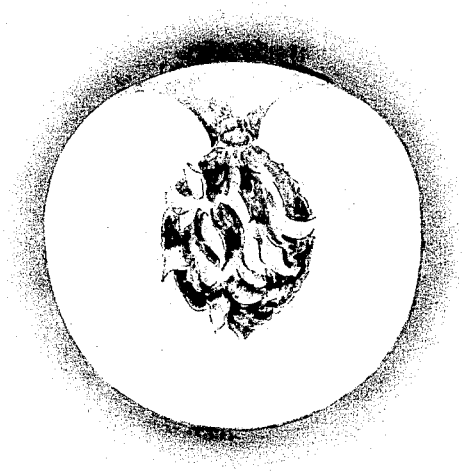
Fig. 2 is a sectional elevation of one of the fruit with the stone exposed.

Referring now more specifically to the pomological details of this new and distanct variety of nectarine tree, the following is an outline description thereof; all major color plate identifications being by reference to Maerz and Paul Dictionary of Color:

Tree:
- *Size.*—Medium.
- *Vigor.*—Medium.
- *Growth.*—Spreading.
- *Production.*—Very productive.
- *Bearing.*—Regular bearer.

Trunk:
- *Size.*—Medium.
- *Texture.*—Medium.

Branches:
- *Size.*—Medium.
- *Texture.*—Medium
- *Lenticels.*—Medium number.

Leaves:
- *Size.*—Large. Average length, 6 to 6½". Average width, 1¾".
- *Thickness.*—Medium.
- *Margin.*—Crenate.
- *Petiole.*—Medium length.
- *Glands.*—Average number—four. Alternate; reniform. Position—usually two on petiole and two or more on blades.
- *Stipules.*—None.
- *Color.*—Top side—medium green (22–L–6). Under side—lighter green (21–J–6).

Flower buds:
- *Size.*—Medium.
- *Length.*—Medium.
- *Form.*—Plump.

Flowers:
- *First and full bloom.*—About with the Elberta peach (unpatented). Medium blooming period as compared with other varieties.
- *Size.*—Large.

Fruit:
- *Maturity when described.*—Eating ripe.
- *Date of first picking.*—July 12, 1955.
- *Date of last picking.*—July 22, 1955.
- *Size.*—Uniform; large. Average diameter axially, 3". Average transversely in suture plane, 3".
- *Form.*—Uniform; globose.
- *Suture.*—Shallow, with slight depression beyond the pistil point.
- *Ventral surface.*—Rounded.
- *Cavity.*—Rounded. Average depth, ⅜". Average breadth, ¾". Markings—red.
- *Base.*—Flat.
- *Apex.*—Short; depressed.
- *Pistil point.*—Lacking.

Skin:
- *Thickness.*—Thick.
- *Texture.*—Tough.
- *Tenacity.*—Tenacious to flesh.
- *Tendency to crack.*—None.
- *Down.*—Wanting.
- *Color.*—Yellow (10–L–7), almost completely overspread with red (3–K–11, shading to 5–L–6, with some mottling, sometimes tending to shade to a deep red (56–L–12).

Flesh:
- *Texture.*—Firm; fine; meaty.
- *Fibers.*—Few.
- *Ripens.*—Even.
- *Flavor.*—Sub-acid.
- *Aroma.*—Wanting.
- *Eating quality.*—Good.
- *Color.*—Yellow (9–J–6, shading to 9–K–8), with red (5–L–6) at stone, becoming lighter (3–L–10) outwardly into flesh.

Stone:

*Type.*—Cling; adheres to flesh over entire surface.

*Size.*—Large to medium. Average length, 1¼″. Average breadth, 1⅛″. Average thickness ¾″.

*Form.*—Globose to oval.

*Base.*—Oblique.

*Hilum.*—Broad; oval.

*Apex.*—Rounded.

*Sides.*—Equa.

*Surface.*—Irregularly furrowed throughout; pitted throughout.

*Ridges.*—Jagged; continuous.

*Ventral edge.*—Thick.

*Dorsal edge.*—Full, with deep groove.

*Tendency to split.*—Very slight.

*Color.*—Dark brown (8–L–7), with reddish (56–L–12) shading.

Use: Market; long distance shipping.

Keeping quality: Good.

Shipping quality: Good.

The tree and its fruit herein described may vary in slight detail due to climatic and soil conditions under which the variety may be grown.

The following is claimed:

A new and distinct variety of nectarine tree, as illustrated and described, characterized by large size, yellow flesh, clingstone fruit whose exterior color is yellow almost entirely over-spread with red; said fruit being further characterized—as compared with the Red Grand nectarine—by ripening approximately two weeks earlier; and additionally characterized—as compared with the Early Le Grand nectarine—by ripening at approximately the same time but bearing fruit slightly smaller in size, more nearly round in shape, smoother in surface, having a more attractive yellow under color, much more red exterior color, more red color next to the stone, less subject to growth cracks and split pits, having a lower chilling requirement, and experiences less bud drop after warm winters, followed by much heavier sets of fruit of more uniform size and shape; and further characterized—as compared with said Early Le Grand nectarine—by shoot growth which is markedly shorter, heavier, and more upright, and leaves which are lighter in color.

No references cited.